United States Patent [19]

Stautzenberger et al.

[11] 4,038,394

[45] July 26, 1977

[54] SUBSTITUTED PYRIMIDO-[4,5-D]-PYRIMIDINE COMPOUNDS USEFUL FOR REPELLING INSECTS, RODENTS OR ANIMALS FROM SUBSTRATES

[75] Inventors: Adin Lee Stautzenberger; Frank Stevens Wagner, both of Corpus Christi, Tex.

[73] Assignee: Celanese Corporation, New York, N.Y.

[21] Appl. No.: 572,532

[22] Filed: Apr. 28, 1975

[51] Int. Cl.$^2$ .............................................. A01N 9/22
[52] U.S. Cl. ...................................... 424/251; 424/30

[58] Field of Search ................................ 424/251, 30; 260/256.4 F

[56] References Cited

U.S. PATENT DOCUMENTS 3,902,846  9/1975  Tracy et al. ............................ 8/184

Primary Examiner—Allen J. Robinson
Attorney, Agent, or Firm—John A. Shedden

[57] ABSTRACT

Pest repellency afforded by the presence of an effective amount of 2,7-dioxo (or dithio) decahydropyrimido-[4,5-d]-pyrimidines; compositions and treatments therewith; and pest repellent structures.

3 Claims, No Drawings

SUBSTITUTED PYRIMIDO-[4,5-D]-PYRIMIDINE COMPOUNDS USEFUL FOR REPELLING INSECTS, RODENTS OR ANIMALS FROM SUBSTRATES

This invention relates to a process of repelling pests, such as insects rodents and animals, with 2,7-dioxo (or dithio) decahydropyrimido-[4,5-d]-pyrimidines.

The chemical control of insects, and other pests, has in recent times undergone substantial reevaluation and the general trend of investigation has been to provide new chemicals which are characterized by low toxicity, particularly with respect to mammals. Even with the newly discovered pesticides of low mammalian toxicity, there still remain considerable shortcomings in that the new compounds have a high kill ratio for the so-called pest insects and at the same time also for non-pest insects. The effects of the widespread use of insecticides, such as DDT, chlordane and similar such commercial pesticides, has justifiably been cause for alarm among botanists, entomologists and others concerned with the ecological consequences of such use.

To preserve the balance necessary to the insect world, it would be more desirable to provide chemicals which repel rather than kill pests as well as non-pest species indiscriminately.

It has now been discovered that the aforesaid pyrimidine compound has surprising repellency for various insects, rodents and animals, but, at the same time, is not fatal to the repelled species. Thus, when tested against various pests, the pyrimidine compound has shown effective repellency but has no pesticidal activity and no serious detectable toxicity for other mammals or non-pest species.

The pyrimidine compounds contemplated by the present invention was represented by the formula:

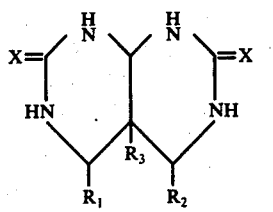

FORMULA I wherein X is S or O; $R_1$ is alkyl, cycloalkylalkyl or aralkyl; $R_2$ is alkyl, cycloalkyl, aryl or aralkyl; and $R_3$ is H, alkyl, cycloalkyl, aryl, or aralkyl, said substituents preferably containing up to about 8 carbon atoms. The said alkyl groups preferably are lower alkyl. The said pyrimidine compounds are prepared by known procedures, the most common of which involves the reaction of an aldehyde with urea, or thiourea, to form the desired compound. When 3 moles of an aldehyde are reacted with 2 moles of the urea compound, in the resulting product, $R_1$ and $R_2$ are the same, and $R_3$ is one —$CH_2$— less than $R_1$ or $R_2$. Thus, where acetaldehyde is the selected aldehyde, in the resulting product, $R_1$ and $R_2$ are each $CH_3$ and $R_3$ is H; with propionaldehyde, $R_1$ and $R_2$ are each ethyl and $R_3$ is methyl; with phenylacetaldehyde, $R_1$ and $R_2$ are each benzyl, and $R_3$ is phenyl, etc. The present pyrimidine compounds can also be prepared by condensation of an aldehyde (e.g. $R_2CHO$) with an appropriately substituted hexahydropyrimidine of the formula:

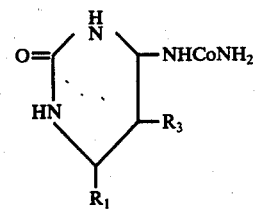

FORMULA II

This procedure may be used to produce compounds in which $R_2$ differs from $R_1$, e.g. benzaldehyde reacts with 2-oxo-4-methyl-6-ureidohexahydropyrimidine to form the product in which $R_1$ is methyl and $R_2$ is phenyl. Similarly, other compounds in which $R_1$ and $R_2$ differ can be prepared. The aforementioned methods are described in U.S. Pat. No. 3,772,292.

Of the aforementioned compounds, the presently preferred is the compound in which $R_1$ and $R_2$ are each methyl and $R_3$ is H, i.e. 2,7-dioxo-4,5-dimethyldecahydropyrimido-[4,5-d]-pyrimidine. The following disclosure specifically illustrates the use of the presently preferred compound, but it should be understood that the compositions, and directions for use should apply to all compounds falling within the ambit of Formula I.

2,7-Dioxo-4,5-dimethyldecahydropyrimido-[4,5-d]-pyrimidine is a known compound and is described in 92 *Monatshefte fur Chemie* 31 (1961). The preparation of this compound is disclosed in copending, and commonly assigned U.S. Pat. application Ser. No. 135,776 filed Apr. 20, 1971 by James E. Tracy, Paul M. Schumacher and Alan L. Peterkofsky, incorporated herein by reference now U.S. Pat. No. 3,902,846. Suitably 5285 parts by weight (120 moles) of acetaldehyde are charged to a suitable conventional reaction vessel and cooled to below 20° C. Then a solution of 3600 parts by weight (60 moles) of urea and 645 parts by weight of reagent grade sulfuric acid (98 percent) in 4275 parts by weight of water are added dropwise with stirring to the acetaldehyde. During the addition, a suitable cooling means (e.g., an ice-bath) is applied to the reaction vessel, and the rate of addition is adjusted, if necessary, in order to maintain the reaction system at a temperature of about 20° C. When the addition is complete, the reaction mixture is heated to atmospheric reflux temperature and maintained thereat for 1 hour. Thereafter, the reaction mixture is cooled to ambient temperature, diluted with water, and filtered to isolate the crystalline product, (A). The product is washed with water, then with methanol, and finally recrystallized from water. After drying the recrystallized product at 70° C., it weighs 1467 parts (25 percent of the theoretical yield based on urea) and melts at 275°–280° C. Elemental analysis of the product corresponds to the formula $C_8H_{14}N_4O_2$.

The process of the present invention is accomplished by merely applying the active agent to a substrate and the substrate then becomes repellent to pests. The active agent can be used alone, but because of its high order of repellency is suitably employed with extending agents, either particulate or liquid, as is convenient for the intended purpose.

The extending agent, of course, will be selected on the basis of the specific application contemplated. Such will include any and all of the usual economically practical, commercially available extending agents conveniently used in the pesticide field. They include, therefore, the solvents of a true solution, the liquid phase of suspensions or aerosols, the semi-solid carrier of ointments and the solid phase of dusts and powders. The extending agents, of course, should be non-toxic especially when employed in agricultural use, and chemically inert to the active agent of this invention.

It has been found that 2,7-dioxo-4,5-dimethyldecahydropyrimido-[4,5-d]-pyrimidine is effective when dispersed in an extending agent at a concentration as little as 0.01 percent by weight. This concentration is effective when the dispersing agent is liquid, but it is usually preferred, although not absolutely essential, to use more concentrated mixtures, for example up to about 5 percent by weight, when the dispersing agent is a semi-solid or a solid. This is because liquid dispersions which are, of course, suitable for use as sprays give more intimate contact of the active material with the substrate and therefore are more effective at lower concentrations. There are a number of liquid media which can be used for the preparation of solutions or suspensions of the active agent. For example, the active agent has a very high order of solubility in water, and polar solvents such as acetone, dioxane and tetrahydrofurane. For certain applications, it may be desirable to use a mixture of solvents such as a water-acetone mixture. If the active agent is to be applied in an aerosol, it is convenient to dissolve it in a suitable solvent and to disperse the resulting solution in a liquid such as butane. For aerosol applications, it has been found that it is better to employ true solutions of the active agents although it is possible to employ suspensions or emulsions.

For use as a powder or a dust, the present active agent can be incorporated in any number of extending agents, either organic or inorganic in nature, which are suitable for the manufacture of pulverulent preparations. These include, for example, calcium carbonate, kaolin, kieselguhr, talc, casein, magnesium carbonate, boric acid and others. Materials of vegetable origin such as powdered chalk, powdered wood and powdered walnut shells are also useful. These compositions may be used in the dry form, or by the addition of wetting agents, the dried powder can be rendered wettable by water so as to be able to obtain stable aqueous dispersions suitable for use as sprays. Foam compositions are also contemplated.

For all of the forms described above, the dispersions may be provided ready for use, or they may be provided in a concentrated form suitable for mixing with other extending agents at the time of application.

When the aforementioned compositions are used especially in agricultural applications, it is advantageous to add other active agents to the compositions described. Such other active agents may include plant growth promoters such as gibberellin along with various nutrients such as organic and inorganic fertilizers, or herbicides, fungicides, insecticides, pesticides or sterilants. The agent of this invention may for example be utilized in conjunction with the anti-mycotic compositions of copending and commonly assigned application Ser. No. 555,927, filed Mar. 6, 1975.

When the present active agent, either alone or in a composition including an extending agent, is applied to a substrate, pests are repelled from the substrate by the active agent. For example, a 0.1 percent aqueous solution of the present active agent when applied to human skin repels mosquitos. A 1 percent acetone solution of the present active agent when applied to a surface renders the surface roach-repellent as evidenced by test data presented in the examples which follow. When surfaces are treated with varying concentrations of the present active material, the extent of repellency of the surface for tests will vary with the concentration of active materials and the species of tests involved, as is recognized by those skilled in the art. The repellency effect is not solely noted with insects in that mammals, such as dogs and cats, react similarly to substrates treated with the present active agent. For example, cats will not eat cat food which has been treated with the active agent of this invention.

The present active agent has been shown to have an extremely high order of repellency against roaches but with no apparent toxic effects on the roaches tested. The repellency is determined using a standard test designed for the specific purpose of such evaluation. In no instance did any of the test roaches die and there were no noticeable toxic effects observed in the test roaches. The effectiveness of the present active agent against rodents is less pronounced than against roaches as determined by standard test procedures. However, there is a noticeable repellent effect against laboratory rats as determined using standard test procedures.

The insecticidal evaluation of the present new agent indicates no apparent insecticidal activity with any of the test species including roaches and Cabbage Looper Larvae at all levels tested. At the same test levels, DDT and chlordane showed a percentage kill of from 0 to 100 percent with both species of insects.

Because of the very high order of solubility of the present active agent in water, aqueous solutions of the active agent are usually preferred, particularly for use in agricultural applications. Such aqueous solutions are readily applied to substrates by the use of spray techniques which are commonly employed in agricultural applications. In particular, aqueous solutions of the present active agent are especially suited for application to the human skin for the general purpose of insect repellency. Such aqueous solutions are especially advantageous in that they are colorless and odorless, and in particular, are non-staining.

Of course, where appropriate the active repellent agent need not be recovered from the preparative reaction system, as where the latter is employed as a vehicle for the repellent, after removal of residual acetaldehyde, if any, and suitable dilution.

The following examples are give by way of illustration of the invention described.

EXAMPLE 1

Roach Repellency

German roaches of mixed age and sex are entered into a glass test chamber 10 × 10 × 24 inches with test panels affixed in the corners where roaches tend to congregate. The test panels are 3 × 5 index cards to which 1 ml. of an acetone solution of 2,7-dioxo-4,5-dimethyldecahydropyrimidino-[4,5-d]-pyrimidine is applied at the indicated concentrations after which the card is air-dried. In all, approximately 200–250 roaches are used in each test. The test chamber is rotated 90° at least once per hour. Periodically, the number of roaches on each panel are recorded to determine repellency.

The results are summarized in Table 1.

TABLE 1

| SOLUTION CONCENTRATION | NUMBER OF ROACHES ON PANEL AT-: | | | | | | | | | | | |
|---|---|---|---|---|---|---|---|---|---|---|---|---|
| | Min. 0:15 | Min. 0:30 | Min. 0:45 | Hr. 1:00 | Hrs. 1:30 | Hrs. 2:00 | Hrs. 2:15 | Hrs. 2:30 | Hrs. 2:45 | Hrs. 3:00 | Hrs. 3:30 | Hrs. 20:00 |
| 5 | 3 | 0 | 0 | 2 | 0 | 0 | 0 | 0 | 0. | 0 | 0 | 2 |
| 2.5 | 3 | 2 | 1 | 0 | 2 | 0 | 0 | 0 | 0 | 1 | 0 | 2 |
| 1.25 | 3 | 2 | 0 | 1 | 0 | 1 | 0 | 0 | 0 | 0 | 0 | 0 |
| CONTROL | 1 | 5 | 6 | 4 | 8 | 11 | 10 | 22 | 9 | 10 | 11 | 30 |

From the data of Table 1, the total number counted for the full period at 5 percent, 2.5 percent and 1.25 percent were 7, 11 and 7 respectively, whereas the control was 127. These determinations show clear cut roach repellency activity of the tested pyrimidine compound.

EXAMPLE 2

The pyrimidine compound of Example 1 was dissolved in water at levels of 5,000, 500 and 50 ppm. and excised Lima Bean leaves were dipped into each test solution and then dried. Larvae of the Cabbage Looper (typical lepidopteraus larvae) were placed on petri dishes with the treated leaves and untreated leaves as control.

The larvae showed an initial reluctance to feed on the treated leaves when compared to the control, but the reluctance diminished after 48 hours.

EXAMPLE 3

The pyrimidine compound of Example 1 in aqueous solution (1 percent) applied externally to human skin was tested against large black mosquitos (indigenous to Corpus Christi, T.x.) and found to have noticable repellency for the mosquitos.

EXAMPLE 4

Insecticidal Evaluation using Roaches Procedure

Medium size roaches were anesthesized by exposure to a constant flow of carbon dioxide and then handled in a conventional manner with small forceps and micro droplets of the tested agent applied to the metathorax region by means of a calibrated micro injection needle. The dosage is expressed in terms of gamma of active ingredient per individual insect. After treatment, the insects are held in pint jars with wire screen top on the surface of which is placed a cotton wad containing a sugar solution.

The roaches are kept under constant observation to record cases of rapid kill with percent mortality values being given at the end of 48 hours. The active agent was administered in the form of an acetone solution.

The results indicate that at a dose of 50, 5 and 0.5 gamma, the pyrimidine compound of Example 1 showed a 0 percent kill after 48 hours whereas chlordane under identical conditions showed a 100 percent kill after 24 hours at the 50 gamma dose; 40 percent at the 5 gamma dose; and 0 percent at the 0.5 gamma dose level.

EXAMPLE 5

Insecticidal Activity with Cabbage Looper Larvae Procedure

The pyrimidine compound of Example 1 was dissolved in water at levels of 5,000, 500 and 50 ppm. and Larvae of the Cabbage Looper were immersed in the test solution. After 48 hours, the percent kill was 0 at all three levels whereas DDT at corresponding levels showed a 100 percent kill after only 24 hours at the 5,000 and 500 ppm. levels and a 60 percent kill at the 50 ppm. level.

It will be appreciated that the dosage of active repellent agent applied to the substrate will be a function of the method of topical application employed. Typically, the treatment composition will be padded or sprayed onto the substrate in such manner as to provide a uniform thin coating thereon. Thus, in the case of an aqueous aerosol application utilizing a concentration of active agent ranging from 0.01 to 3.0 percent by weight, the surface would be rendered visibly wetted without excess. The use of such low concentrations is particularly preferred where repeated applications may be desirable to initiate or retain effectiveness.

EXAMPLE 6

The procedure of Example 1 is repeated using in lieu of the described pyrimidine compound, each of the following compounds of Formula I:

| | $R_1$ | $R_2$ | $R_3$ | X |
|---|---|---|---|---|
| a | $C_2H_5$ | $C_2H_5$ | $CH_3$ | S |
| b | $CH_3$ | $C_6H_5$ | H | O |
| c | $CH_3$ | $C_6H_{11}$ | H | O |
| d | $C_6H_{11}CH_2$ | $CH_3$ | $C_6H_{11}$ | S |
| e | $C_6H_5CH_2$ | $C_2H_5$ | $C_6H_5$ | O |
| f | $C_2H_5$ | $C_3H_7$ | $CH_3$ | O |
| g | $CH_3$ | $C_6H_5CH_2CH_2$ | H | O |
| h | $CH_3$ | $CH_3$ | H | S |

Comparable results are obtained.

What is claimed is:

1. A method for repelling insects, rodents or animals from a substrate which comprises applying to said substrate a repellent effective amount of a pyrimidine compound of the formula:

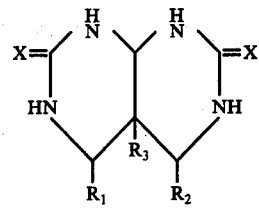

wherein X is S or O; $R_1$ is alkyl, cycloalkylalkyl or aralkyl; $R_2$ is alkyl, cycloalkyl, aryl or aralkyl; and $R_3$ is H, alkyl, cycloalkyl, aryl or aralkyl; each hydrocarbon radical containing up to about 8 carbon atoms.

2. The method as in claim 1 wherein said pyrimidine compound is 2,7-dioxo-4,5-dimethyldecahydropyrimido-[4,5-d]-pyrimidine.

3. The method of claim 2, wherein said pyrimidine compound is dispersed in an extending agent at a concentration of 0.01 to 5.0 percent by weight.

* * * * *